United States Patent [19]

Bauer et al.

[11] 4,188,227
[45] Feb. 12, 1980

[54] METHOD OF PREPARING MULTI-COMPONENT CHEMICAL COMPOSITIONS

[76] Inventors: Randy L. Bauer, 4606 Sixth Ave., Vienna, W. Va. 26105; Gerald A. Krulik, Rte. 1, Box 212, Washington, W. Va. 26181

[21] Appl. No.: 801,185

[22] Filed: May 27, 1977

[51] Int. Cl.$^2$ .................... C09D 5/20; C09K 3/00; C09K 3/18

[52] U.S. Cl. ................... 106/1.27; 106/1.05; 106/1.25; 106/1.29; 106/74; 106/308 N; 106/308 Q; 106/308 S

[58] Field of Search .................. 106/1.27, 1.25, 1.29, 106/1.05, 74, 308 Q, 308 N, 308 S

[56] References Cited

U.S. PATENT DOCUMENTS

| | | | |
|---|---|---|---|
| 3,152,009 | 10/1964 | De Long | 106/1.27 X |
| 3,211,578 | 10/1965 | Gutzeit | 106/1.27 X |
| 3,279,998 | 10/1966 | Raff et al. | 424/19 |
| 3,281,266 | 10/1966 | Colonel | 106/1.27 X |
| 3,420,680 | 1/1969 | Gulla | 106/1.27 X |
| 3,565,823 | 2/1971 | Parshall | 252/429 |
| 3,586,524 | 6/1971 | Richardson | 106/1.27 X |
| 3,717,482 | 2/1973 | Gulla et al. | 106/1.27 X |
| 3,719,508 | 3/1973 | Gulla et al. | 106/1.27 |
| 3,876,434 | 4/1975 | Dulkewych et al. | 106/1.27 |
| 4,038,085 | 7/1977 | Scannell | 106/1.27 |

*Primary Examiner*—Helen M. S. Sneed
*Attorney, Agent, or Firm*—Fay & Sharpe

[57] ABSTRACT

A method of preparing compositions having two or more components, without producing a direct combination reaction, by adding one or more constituents to a molten hydrated salt having a melting point below about 100° C. then cooling the product to obtain a homogeneous, uniformly dissoluble composition.

10 Claims, No Drawings

METHOD OF PREPARING MULTI-COMPONENT CHEMICAL COMPOSITIONS

CROSS REFERENCE TO RELATED APPLICATION

In co-pending application, U.S. Ser. No. 574,498 filed on May 5, 1975 by Jameson et al, and assigned to the same assignee as the present application, there is described a method of preparing catalysts in which noble metal salts are reacted with a low melting tin salt.

BACKGROUND OF THE INVENTION

1. Field of the Invention

Methods of preparing homogeneous, multi-component compositions.

2. Description of the Prior Art

U.S. Pat. No. 3,876,434 (Dutkewijch et al) describes some of the problems of attempting to replenish aqueous solutions, in this case electroless plating solutions, from the dry materials. The inventors recognize that localized concentrations of certain of the constituents may cause decomposition of the plating bath.

U.S. Pat. No. 3,565,823 (Parshall) describes catalytic materials containing metal halides dispersed in a molten halostannate or halogermanate composition. In this case, the molten salt is not hydrated.

U.S. Pat. No. 3,279,998 (Raff et al) describes a method in which medicaments are added to a molten wax such as paraffin, or fatty acid esters such as stearyl palmitate. The medicaments are mixed into the molten mass and then the mixture is congealed and comminuted into powder for subsequent tablet manufacture.

In the aforementioned application Ser. No. 574,498 a palladium double salt is reacted with a molten tin salt producing a direct combination reaction.

SUMMARY OF THE INVENTION

The present invention relates to methods of manufacturing multi-component mixtures of various materials in an energy saving manner. When one considers that a great many compounds are sold simply as intimate mixtures of two or more dry compositions, it should be recognized that the uniformity of any isolated sample of such material is inherently rather poor. Because of differences in particle size, shape and density, the fine particles will sift to the bottom of the container during shipping and storage; and the larger particles will remain at the top. Thus, if one wishes to obtain an uniform sample, the product must be mixed again immediately prior to its use.

Uniformity from portion to portion is especially critical in the replenishing of aqueous solutions with solid materials to be dissolved in the same. As Dutkewijch points out, in the replenishment of electroless plating baths, high, localized concentration and/or imbalances between two or more constituents may cause spontaneous decomposition.

One common way of manufacturing homogeneous mixtures is to make-up an aqueous solution of several components and then drive off the water, such as by spray drying. This is enormously wasteful of energy since for each pound of water one must add about 144 BTU's plus the sensible heat required to bring the liquid material up to the boiling point thereof.

In the present invention, it is proposed to use, as a solvent for other components, a hydrated salt having a melting point below about 100° C. The molten salt may be employed simply as a carrier having no utility other than as a vehicle or it may constitute an active ingredient in the mixture.

In addition to the energy saving aspects of this invention one can obtain completely homogeneous, stable and uniformly dissoluble compositions containing a variety of ingredients with varying solubility and other characteristics. It is important to note that no direct combination reaction occurs in this reaction although it is quite possible, indeed probable, that a double decomposition, sometimes referred to as double replacement or metathesis does occur. For example, mixtures of $ab+cd$ will result in some $ac+bd$ being produced.

In copending application Ser. No. 574,498 filed May 5, 1975 by Jameson et al, and owned by the same assignee as the present invention, there is described a direct combination reaction in which palladium chloride, as a double salt mixture, is added to a molten stannous chloride bath. In this case a reaction takes place which is a direct combination resulting in a complex or colloid being formed. Reactions to the type are not pertinent to the present invention. For additional information on different types of basic reactions, refer to Encyclopedia of Chemistry, Hampel & Hawley, 3rd Ed., Van Nostrand (1973) pp. 954–955.

In general, the present invention is directed to a new method of making complex mixtures of inorganic and/or organic concentrates comprising the steps of selecting an appropriate hydrated salt of an inorganic or organic composition with a suitable low melting point to serve as a solvent for other components; melting the hydrated salt; adding other components to the "solvent"; mixing and reacting the ingredients to form a homogeneous mixture; allowing the molten salt mixture to cool and solidify; and then converting the solidified mixture to a convenient form, such as powder pellets or tablets.

Summarizing the advantages, it can be readily appreciated that the processing costs are considerably lower than by conventional evaporation or spray drying methods. It takes considerably less energy to melt the salt then it does to drive off a quantity of water sufficient to dissolve the original constituents. In addition, no bulky, aqueous solutions need be prepared, processed or stored. These solutions are subject to crystallization should the temperature drop, or if the wrong amount or balance of solutes are mixed, thus leading to a non-homogeneous system. The resulting product is essentially a homogeneous solid which will dissolve more uniformly than a physical mixture, and being a homogeneous solid it will not segregate into different layers of compositions during shipment and storage. This phenomenon is common where physical mixtures have components of different particle size, shape and/or density.

Examples of this process is useful for virtually any type of mixture including pharmaceuticals, detergent and other cleaning compounds, food products, dry additives for chemical processing and the preparation of dry compositions for plating solutions. The latter is quite important because of the difficulty in replenishing plating baths. The localized concentration or imbalance of two or more constituents added to the bath can have disasterous consequences. By assuring a uniform and homogeneous mixture, these problems are virtually eliminated.

Examples of hydrated salts which are useful in the process, but in no way limiting of the disclosure are the following: aluminum nitrate monohydrate, aluminum ammonium sulfate dodecahydrate, ammonium cerous nitrate tetrahydrate, barium hydroxide octahydrate, barium iodide hexahydrate, cadmium chlorate dihydrate, cadmium nitrate tetrahydrate, calcium bromide trihydrate, calcium bromide hexahydrate, calcium chloride hexahydrate, calcium iodide hexahydrate, calcium nitrate trihydrate, calcium nitrate tetrahydrate, cesium aluminum sulfate dodecahydrate, chromic chloride hexahydrate, chromic nitrate monahydrate, chromic sulfate.15$H_2O$, cobalt bromide hexahydrate, cobaltous chlorate hexahydrate, cobaltous chloride hexahydrate, cobaltous nitrate hexahydrate, cobalt sulfate septahydrate, copper acetate monohydrate, copper chlorate hexahydrate, copper nitrate trihydrate, ferric bromide hexahydrate, ferric chloride hexahydrate, ferrous iodide pentahydrate, ferric nitrate hexahydrate, ferric sulfate septahydrate, lead acetate decahydrate, lithium acetate dihydrate, lithium metaborate octahydrate, lithium bromide dihydrate, lithium perchlorate trihydrate, magnesium acetate tetrahydrate, magnesium chlorate hexahydrate, magnesium nitrate hexahydrate, manganese chloride tetrahydrate, manganese nitrate hexahydrate, nickel chloride hexahydrate, nickel nitrate hexahydrate, nickel sulfate hexahydrate, potassium aluminum sulfate dodecahydrate, potassium chromic sulfate dodecahydrate, potassium fluoride dihydrate, potassium ferric sulfate dodecahydrate, sodium potassium tartrate tetrahydrate, sodium acetate trihydrate sodium aluminum sulfate dodecahydrate, sodium metaborate tetrahydrate, sodium tetraborate decahydrate, sodium carbonate decahydrate, sodium hypochlorite dihydrate, sodium formaldehyde sulfoxylate dihydrate, sodium orthophosphate dodecahydrate, sodium metasilicate monahydrate, sodium sulfate decahydrate, sodium hydrogen sulfate monohydrate, sodium thiosulfate pentahydrate, stannous chloride dihydrate, stannic chloride trihydrate, zinc bromate hexahydrate, zinc nitrate trihydrate, zinc nitrate hexahydrate, tartaric dibenzoate monohydrate, tetraethyl ammonium acetate.4$H_2O$, tetraethyl ammonium chloride monohydrate, tetraethyl ammonium hydroxide.5$H_2O$, trimethyl amine N oxide.2$H_2O$, benzene sulfonic acid monohydrate, and other such compounds.

DETAILED DESCRIPTION OF THE INVENTION

In order to best understand the principles of the present invention, the following examples are set forth which are intended to be illustrative only:

EXAMPLE I

A sample of 424 g. $Na_2CO_3.10H_2O$ was melted in a flask. To this molten salt was added 1564 g. sodium hypophosphite monohydrate. The two components mixed together easily to form a homogeneous solution. The molten mass was poured into a tray and quickly solidified to a hard, dry, homogeneous solid.

EXAMPLE II

A sample of 191 g. $Na_2CO_3.10H_2O$ was melted in a flask. To this molten salt was added 224 g. trisodium citrate dihydrate and 164 g. NaCl. The mixture was stirred until homogeneous and poured into a tray. It rapidly cooled to a hard, dry, homogeneous solid.

EXAMPLE III

A sample of 300 g. $NiCl_2.6H_2O$ was melted in a large flask. To this molten salt was added 122 g. $NiSO_4.6H_2O$, 27.6 g. $(NH_4)_2H$ citrate, 202 g. ammonium chloride, 281 g. ammonium hypophosphite, and 1438 g. sodium hypophosphite dihydrate. The molten salt mixture was stirred until the solution was homogeneous. It was then poured into a tray where it is cooled to a hard, yellow green, homogeneous solid.

The ammonium chloride is principally a complexing agent, forming nickel amine complexes in solution; but to some degree it also acts as a buffer. The ammonium citrate is primarily a buffer, but also functions as a complexing agent.

EXAMPLE IV

A sample of 300 g. $NiCl_2.6H_2O$ was melted in a large flask. To this molten salt was added 122 g. $NiSO_4.6H_2O$ and 35.9 g. trisodium citrate hydrate. The mixture was stirred until homogeneous and poured into a tray to cool. The product was a hard, homogeneous mass.

EXAMPLE V

The dry solids obtained from Examples I and IV were added in the appropriate amounts directly to an electroless nickel working bath. This bath is typical of alkaline room temperature electroless nickels (Borg-Warner Corporation N-35 electroless nickel). The two solid components contained nickel salts and hypophosphite salts to replenish the compounds used up in electroless plating, and the buffers and pH adjusters to maintain bath stability. The two solids dissolved easily and uniformly without causing working bath decomposition.

EXAMPLE VI

A cleaning composition may be prepared by melting 500 gm. of sodium carbonate decahydrate, 100 gm. sodium pyrophosphate.12$H_2O$, 50 gm. sodium metasilicate monohydrate; and 100 gm. sodium citrate. All of the above are intimately mixed and the resulting mass is allowed to cool and congeal. It may then be ground to a powder.

EXAMPLE VII

A medicinal preparation may be prepared by melting 10 gm. of sodium sulfate decahydrate and adding 1 gm. of sodium acetyl salicylate (aspirin). After mixing, the composition may be poured into a mold having a plurality of tablet cavities and allowed to cool. The concentration of aspirin may be adjusted to proper dosage.

While this invention has been described in connection with certain specific embodiments thereof, it is to be understood that this is by way of illustration and not by way of limitation; and the scope of the appended claims should be construed as broadly as the prior art will permit.

What is claimed is:

1. A process for preparing a multicomponent chemical composition including an unreacted hydrated salt and a complexing agent comprising the steps of: (1) melting a hydrated salt which has a melting point below about 100° C.; (2) adding a complexing agent to the molten salt, said complexing agent being incapable of a direct combination reaction with said hydrated salt; (3) mixing said complexing agent into said molten salt to form a homogeneous mass; and (4) cooling said mass to solidify the resulting product.

2. A process as defined in claim 1 wherein said hydrated salt is an inert vehicle for other constituents in the resulting product.

3. A process as defined in claim 1 wherein said hydrated salt is an active constituent in the resulting product.

4. A process as defined in claim 1 wherein a plurality of different hydrated salts are melted as the initial step.

5. A dry, homogeneous composition comprising an unreacted mixture of a hydrated nickel salt having a melting point below about 100° C. and a complexing agent, said homogeneous composition being obtained by: (1) melting said hydrated nickel salt; (2) adding said complexing agent to said molten hydrated nickel salt without causing said salt and said complexing agent to react with each other; (3) mixing said complexing agent into said salt to form a homogeneous mass; and (4) cooling said mass to solidify the resultant product.

6. Composition mixture as defined in claim 5 additionally containing a reducing agent.

7. A composition as defined in claim 6 wherein said reducing agent is a hypophosphite.

8. A composition as defined in claim 5 wherein said complexing agent is ammonium chloride.

9. A composition as defined in claim 5 additionally containing a buffering agent.

10. A composition as defined in claim 9 wherein said buffering agent is ammonium citrate.

* * * * *

UNITED STATES PATENT AND TRADEMARK OFFICE
CERTIFICATE OF CORRECTION

PATENT NO. : 4,188,227
DATED : February 12, 1980
INVENTOR(S) : Randy L. Bauer and Gerald A. Krulik It is certified that error appears in the above—identified patent and that said Letters Patent is hereby corrected as shown below:

In the patent heading, the following patent assignment data is added following the line identified as [76] Inventor:

Assignee: McGean Chemical Company, Inc.
                Cleveland, Ohio

Signed and Sealed this

*Twenty-second* Day of *July 1980*

[SEAL]

*Attest:*

SIDNEY A. DIAMOND

*Attesting Officer*      *Commissioner of Patents and Trademarks*